United States Patent
Berlanda et al.

(10) Patent No.: US 11,241,470 B2
(45) Date of Patent: Feb. 8, 2022

(54) PHASEOLUS VULGARIS EXTRACTS, THEIR USE AND FORMULATIONS CONTAINING THEM

(71) Applicant: INDENA S.P.A., Milan (IT)

(72) Inventors: Davide Berlanda, Milan (IT); Marco Bertani, Milan (IT); Ezio Bombardelli, Pavia (IT); Andrea Gardi, Milan (IT); Cesare Ponzone, Milan (IT); Fabio Donzelli, Milan (IT)

(73) Assignee: INDENA S.P.A., Milan (IT)

( * ) Notice: Subject to any disclaimer, the term of this patent is extended or adjusted under 35 U.S.C. 154(b) by 593 days.

(21) Appl. No.: 15/643,900

(22) Filed: Jul. 7, 2017

(65) Prior Publication Data

US 2017/0333508 A1 Nov. 23, 2017

Related U.S. Application Data

(62) Division of application No. 12/158,063, filed as application No. PCT/EP2006/012012 on Dec. 13, 2006, now abandoned.

(30) Foreign Application Priority Data

Dec. 22, 2005 (IT) .......................... MI2005A002450

(51) Int. Cl.
*A61K 36/48* (2006.01)
*A23L 33/105* (2016.01)

(52) U.S. Cl.
CPC ............ *A61K 36/48* (2013.01); *A23L 33/105* (2016.08)

(58) Field of Classification Search
None
See application file for complete search history.

(56) References Cited

U.S. PATENT DOCUMENTS

| 7,553,502 B2 | 6/2009 | Bombardelli et al. |
| 7,887,854 B2 | 1/2011 | Bombardelli et al. |
| 2004/0131749 A1* | 7/2004 | Grabiel ............... C07D 311/30 426/629 |

FOREIGN PATENT DOCUMENTS

JP 06116197 4/1994

OTHER PUBLICATIONS

Tormo et al., Hypoglycaemic and anorexigenic activities of an alpha-amylase inhibitor from white kidney beans (*Phaseolus vulgaris*) in Wistar rats, 2004, British J Nutrition, 92: 785-790.*

* cited by examiner

*Primary Examiner* — Terry A McKelvey
*Assistant Examiner* — Catheryne Chen
(74) *Attorney, Agent, or Firm* — Porzio Bromberg & Newman P.C.

(57) ABSTRACT

Extract obtainable by extraction from *Phaseolus* sp. with mixtures of ethanol and water, characterised by an α-amylase inhibitor content in between 1,000 and 1,600 USP/mg (HPLC titre between 6 and 14% w/w) and a phytohaemagglutinin content in between 8,000 and 30,000 HAU/g, and a process for its preparation.

18 Claims, No Drawings

PHASEOLUS VULGARIS EXTRACTS, THEIR USE AND FORMULATIONS CONTAINING THEM

SUMMARY OF THE INVENTION

This invention relates to extracts obtained from the seeds of plants of the genus *Phaseolus*, and the process for the preparation thereof.

More particularly, this invention relates to extracts of *Phaseolus vulgaris* seeds, characterised by a content in α-amylase inhibitors and phytohaemagglutinins in established ratios which reduce the absorption of glucose originating from starches in the diet, and reduce the appetite after repeated administration.

PRIOR ART

α-Amylase inhibitor (αAI) is a glycoprotein contained in the seeds of kidney beans (*Phaseolus vulgaris*) which inhibits the enzymatic activity of amylase of animal origin, and especially human amylase, in a differentiated, species-dependent way. This inhibitor, which was purified for the first time by Marshall and Lauda in 1974 (J. Biol. Chem., 250 (20), 8030-8037, 1975), has attracted interest because of the effects which its pancreatic amylase inhibiting activity can exert on the intestinal absorption of glucose (deriving from enzymatic hydrolysis of starch), and above all for its potential application in the diet industry. Carbohydrates are an important source of calories and contribute to the synthesis of fats in individuals that are predisposed to obesity or Type II diabetes. In nature, in the evolution of the species, the availability of food for survival was intermittent, so the ability to accumulate energy in excess of the amount required for immediate use was essential. The adipose cells, developed in different parts of the body, are among the sites where energy is accumulated, so that it is easily available when the body needs it. This physiological system, orchestrated by endocrine and neurone secretions, enables humans to survive for long periods, even in the absence of food. However, in the event of abundant food, sedentary lifestyle and genetic reasons associated with the lifestyles of industrialised countries, the system increases uncontrollably the adipose energy deposits with adverse consequences, such as beauty flaw, followed by an overload of the cardiocirculatory system. One of the main problems is obesity, which has reached high levels in some countries, such as the United States of America. Obesity is the primary cause of cardiovascular disease, hypertension and diabetes. Excess weight, which is common among both men and women, causes the subject to eat larger and larger amounts of food, and the result is a deterioration in health. As excess blood glucose leads to an increase in energy deposits, the availability of substances that reduce glucose absorption is very important.

Worldwide demand for anti-obesity substances has led to research and study of foods that counteract the progressive body weight accumulation.

α-Amylase inhibitors have long been identified in different legumes and corn, and specific clinical trials have been conducted in last years, with mixed results. Depending on the preparation process used for the concentration and isolation of these inhibitors, the results have been contradictory, as many commercial preparations proved to lack effective activity in vivo. According to the first studies of Layer, Carlson and Di Magno (Gastroenterology, 88(6): 1895, 1902, 1985), this problem is apparently due to the high degree of dilution of the inhibitor in highly impure preparations; in fact, preparations of purified inhibitor are proved to be active on α-amylase when are directly introduced into the intestinal lumen.

The fragmentary processes described in the literature for the preparation of α-amylase inhibitors involve the extraction with phosphate buffer and the insolubilisation of proteins with ammonium sulphate, and do not provide any selectivity. The obtained extracts contain high concentrations of phytohaemagglutinins, and must be diluted to obtain extracts with an acceptable level of toxicity. Apart from the biological aspect, known processes include some stages which make difficult to prepare a product that is both active and safe. The problems that arise during extraction with buffers of different ionic strengths and pH are due to the high concentration of protein and polysaccharide contaminants, which make them highly viscous, leading to problems of low filterability and longer processing times. As these are aqueous extractions, there is also a high risk of microbial contamination of the protein extract, which is difficult to control, especially in the case of highly viscous preparations. All these conditions lead to a loss of product and make difficult to obtain final extracts with a low phytohaemagglutinin titre and the corresponding multicomponent standardisation. Various processes have been used to solve the problem of limiting phytohaemagglutinins, including heat treatments, which lead to the breakdown not only of phytohaemagglutinins, but also of α-amylase inhibitors, with the result that the obtained products are scarcely active. In practice, the products on the market have a very low αAI content. Other products which are too highly enriched in α-amylase inhibitors cause unpleasant problems of flatulence when administered in large doses.

DESCRIPTION OF THE INVENTION

The products according to the invention are prepared by extraction with an aqueous or hydroethanolic medium and precipitation with suitable mixtures of ethanol and water.

It has surprisingly been found that the use of hydroethanolic mixtures on suitably concentrated aqueous extracts of kidney bean produces enriched extracts with an α-amylase inhibitor content having an activity of between 1,000 and 1,600 USP/mg (HPLC titre of between 6 and 14% w/w) and a phytohaemagglutinin content in between 8,000 and 30,000 HAU/g, so that it can be formulated in products for diet use at sufficiently low doses to obtain the desired result. In addition to this major advantage, the process to which the invention relates produces a significant reduction in the microbe count. Another considerable advantage is the possibility of obtaining an end product enriched in (αAI) inhibitor, with defined phytohaemagglutinin ratios.

The process of the invention comprises extraction of the biomass with buffers having a pH ranging between 3 and 6.5, preferably pH 3.5-5.5, and even more preferably pH 4, at temperatures of between 2 and 25° C., and preferably between 4 and 18° C., and subsequent separation of the extract from the biomass by centrifugation.

Suitable buffers for the extraction are typically phosphate, citrate or acetate buffers or dicarboxylic aminoacid buffers, preferably phosphate or citrate buffer. Buffered water-alcohol mixtures can also be used as extraction solvent.

Depending on the used extractors and on the extraction cycle, 5 to 20 volumes of buffer per part of drug are used, preferably 10-12.5 parts, and the mixture is stirred for 1-4 hours, preferably 2 hours; the biomass can be further extracted three more times with a suitable quantity of buffer, and in any case until its α-amylase inhibitor and phytohaemagglutinin content is exhausted.

The combined extracts are clarified by filtration or centrifugation and concentrated in vacuum at a temperature of between 25° and 35° C., preferably 30° C., or by ultrafiltration (10,000 Da cut-off) to a volume corresponding to approx. 10% of the weight of the extract after centrifugation.

The concentrated aqueous extract is then precipitated with ethanol added to a final concentration of between 60 and 70% v/v, preferably 65% v/v, operating at a temperature of between 18° and 30° C., and preferably between 20° and 25° C.

The obtained precipitate can be centrifuged and/or filtered, redissolved in demineralised water and re-precipitated in 60% ethanol to reduce the saline part. Alternatively, it can be diafiltered through a membrane with a 10,000 Da cut-off. The sediment of the precipitation, which constitutes the extract according to the invention, is dried.

If these processes are used, an extract with the following characteristics can be obtained:
HPLC titre: ≥6%≤14% w/w
α-amylase inhibiting activity: ≥1,000≤1,600 USP/mg
haemagglutinating activity: ≥8,000≤30,000 HAU/g The efficacy of the extracts has been proved in rats treated with doses of 200 and 400 mg/Kg a day, with free access to the food consisting of a special starch-enriched diet. During the treatment the extracts according to the invention reduce food consumption significantly, while water consumption remains unchanged.

The product according to the invention is perfectly tolerated, and can be incorporated into pharmaceutical or diet formulations at doses ranging between 50 and 1.000 mg, to be taken at main meals. The extract can be incorporated in drinkable forms or the like, to be taken as appetite suppressants.

The examples below set out illustrate the preparation and the advantages of the invention.

Example 1: Preparation of a Kidney Bean Extract Enriched with αAI Obtained by Extraction with Citrate Buffer and Precipitation with Ethanol A suspension of 150 g of kidney bean flour in 1.5 L of citric acid 5.75 g/L was stirred for 3 hours at +4° C.

The suspension was centrifuged, and the aqueous centrifugate was concentrated 7.5 times (dry residue: 15.0% w/w). The concentrate was diluted with 95% ethanol to a concentration of 65% ethanol to obtain a precipitate which was recovered by centrifugation at +22° C. The collected solid was dried under vacuum at a temperature not exceeding 50° C. The obtained product (yield 2.36%) has an α-amylase inhibiting activity of 1.050 U/mg, a haemagglutinating activity of 9,000 HAU/g, and an HPLC titre of 7.3% w/w.

Example 2: Preparation of a Kidney Bean Extract Enriched with αAI Obtained by Extraction with Citrate Buffer and Precipitation with Ethanol A suspension of 150 g of kidney bean flour in 1.5 L of citric acid 5.75 g/L was stirred for 2 hours at +22° C.

The suspension was centrifuged, and the aqueous centrifugate was concentrated 10.5 times (dry residue: 17.1% w/w). The concentrate was diluted with 95% ethanol to a concentration of 65% ethanol to obtain a precipitate which was recovered by centrifugation at +22° C. The collected solid was dried under vacuum at a temperature not exceeding 50° C. The obtained product (yield 3.5%) has an α-amylase inhibiting activity of 1,600 U/mg, a haemagglutinating activity of 18,600 HAU/g and an HPLC titre of 10.0% w/w.

Example 3: Preparation of a Kidney Bean Extract Enriched with αAI Obtained by Double Extraction with Water-Alcohol Solution (30% Ethanol) of Citric Acid and Precipitation with Ethanol A suspension of 100 g of kidney bean flour in 1.0 L of a 70:30 mixture of water and ethanol, containing citric acid 4.6 g/L, was stirred for 2 hours at +22° C.

The suspension was centrifuged, the clear liquid phase discarded, and the sediment subjected to a new extraction cycle with 750 mL of water. The liquid phase of the second extraction was combined with the first, and concentrated 4.3 times (dry residue: 4.78% w/w). The concentrate was diluted with 95% ethanol to a concentration of 70% ethanol to obtain a precipitate which was recovered by centrifugation at +22° C. The collected solid was dried under vacuum at a temperature not exceeding 50° C. The obtained product (yield 0.88%) has an α-amylase inhibiting activity of 1,570 U/mg, a haemagglutinating activity of 27,000 HAU/g, and an HPLC titre of 13.6% w/w.

The invention claimed is:

1. A process for the preparation of an extract which comprises the steps of:
    a) extraction of *Phaseolus* sp. with aqueous buffers having a pH ranging between 3 and 6.5, and subsequent separation of the extract from the biomass;
    b) extraction of the biomass after step a), and resulting extracts are combined with the extract from the biomass of step a) to form combined extracts;
    c) filtration or centrifugation of the combined extracts, and concentration to a volume corresponding to approx. 10% of the weight of the extract after centrifugation to form a concentrated aqueous extract;
    d) differential precipitation of the concentrated aqueous extract with diluted ethanol, at a final alcohol concentration of between 60 and 70% v/v; and
    e) separation of precipitate and re-precipitation from demineralised water with ethanol, or diafiltration through a membrane with a 10,000 Da cut-off, and drying of precipitation residue,
    wherein the extract comprises an α-amylase inhibitor content in between 1,000 and 1,600 USP/mg corresponding to a content in between 6% and 14% w/w as calculated by HPLC and a phytohaemagglutinin content in between 8,000 and 30,000 HAU/g.

2. The process as claimed in claim 1, wherein phosphate, citrate or acetate buffers, dicarboxylic aminoacid buffers, or buffered water-alcohol solutions are used.

3. The process as claimed in claim 1 further comprising:
    repeating the extraction of step b with the buffer until the α-amylase inhibitors and phytohaemagglutinins are exhausted.

4. The process as claimed in claim 1 wherein the pH has a range between 3.5 and 5.5.

5. The process as claimed in claim 1 wherein the ethanol used in step e is 60% ethanol.

6. The process as claimed in claim 1 wherein step a is performed at a temperature between 2° and 25° C.

7. The process as claimed in claim 1 wherein step c is performed at a temperature between 25° and 35° C.

8. The process as claimed in claim 1 wherein step e is performed at a temperature between 18° and 30° C.

9. The process as claimed in claim 3 wherein the extraction of step b is repeated three times.

10. The process as claimed in claim 1 wherein the extraction of step b is further repeated up to three more times.

11. The process as claimed in claim 3 wherein the extraction of step b is further repeated up to three more times.

12. A process for the preparation of an extract which consists essentially of the steps of:
   a) extraction of *Phaseolus* sp. with aqueous buffers having a pH ranging between 3 and 6.5, and subsequent separation of the extract from the biomass;
   b) extraction of the biomass of step a), and resulting extracts are combined with the extract from the biomass of step a) to form combined extracts;
   c) filtration or centrifugation of the combined extracts of step b, and concentration to a volume corresponding to approx. 10% of the weight of the extract after centrifugation to form a concentrated aqueous extract;
   d) differential precipitation of the concentrated aqueous extract of step c with diluted ethanol, at a final alcohol concentration of between 60 and 70% v/v to form a precipitate; and
   e) separation of the precipitate and re-precipitation from demineralised water with ethanol, or diafiltration through a membrane with a 10,000 Da cut-off, and drying of precipitation residue,
   wherein the extract comprises an $\alpha$-amylase inhibitor content in between 1,000 and 1,600 USP/mg corresponding to a content in between 6% and 14% w/w as calculated by HPLC and a phytohaemagglutinin content in between 8,000 and 30,000 HAU/g.

13. The process as claimed in claim 12, wherein phosphate, citrate or acetate buffers, dicarboxylic aminoacid buffers, or buffered water-alcohol solutions are used.

14. The process as claimed in claim 12 wherein the pH has a range between 3.5 and 5.5.

15. The process as claimed in claim 12 wherein the ethanol used in step e is 60% ethanol.

16. The process as claimed in claim 12 wherein step a is performed at a temperature between 2° and 25° C.

17. The process as claimed in claim 12 wherein step c is performed at a temperature between 25° and 35° C.

18. The process as claimed in claim 12 wherein step e is performed at a temperature between 18° and 30° C.

* * * * *